United States Patent [19]
Calello et al.

[11] Patent Number: 6,086,859
[45] Date of Patent: Jul. 11, 2000

[54] METHOD FOR TREATING CHAPPED LIPS

[75] Inventors: Joseph Frank Calello, Union; Janet Elizabeth Opel, Brick; Renée Joan Ordino, Edison; Robert Walter Sandewicz, Spotswood, all of N.J.; Natividad R. Jose, Jamaica, N.Y.

[73] Assignee: Revlon Consumer Products Corporation, New York, N.Y.

[21] Appl. No.: 08/980,431

[22] Filed: Nov. 28, 1997

Related U.S. Application Data

[63] Continuation-in-part of application No. 08/918,134, Aug. 27, 1997.

[51] Int. Cl.$^7$ ............................................. A61K 7/027
[52] U.S. Cl. .......................... 424/64; 424/63; 424/401; 424/DIG. 5
[58] Field of Search ................. 424/401, 64, DIG. 5, 424/63

[56] References Cited

U.S. PATENT DOCUMENTS

| | | |
|---|---|---|
| 4,866,202 | 9/1989 | Weil ........................................ 560/180 |
| 5,200,172 | 4/1993 | Kamen . | |
| 5,597,813 | 1/1997 | Blank . | |
| 5,776,441 | 6/1998 | Scancarella et al. ..................... 424/61 |

OTHER PUBLICATIONS

Blistex, Lip Tone, Lip Balm : Package copy : Jan. 1996.
Federal Register, vol. 48, No. 32, Proposed Rules, Feb. 1983.
CTFA Labeling Manual, A Guide to Labeling and Advertising Cosmetics and OTC Drugs, Sixth Edition, 1997, p. 114.

*Primary Examiner*—Jyothsna Venkat
*Attorney, Agent, or Firm*—Julie Blackburn

[57] ABSTRACT

A method for preventing, retarding, arresting, or reversing the effects of chafed, chapped, cracked, or windburned lips comprising applying to the lips a pigmented lipstick composition comprising, by weight of the total composition:

- 0.01–30% skin protectant selected from the group consisting of allantoin, cocoa butter, dimethicone, glycerin, petrolatum, shark liver oil, and mixtures thereof,
- 1–25% pigment,
- 5–80% of an oil selected from the group consisting of nonvolatile oil, volatile oil, and mixtures thereof, and
- 3–40% of a wax having a melting point of 30 to 135° C.

8 Claims, No Drawings

METHOD FOR TREATING CHAPPED LIPS

This application is a continuation-in-part of U.S. patent application Ser.No. 08/918,134, filed Aug. 27, 1997, which is hereby incorporated by reference in its entirety.

TECHNICAL FIELD

The invention is in the field of pigmented cosmetic stick compositions for applying to lips to treat chapped, chafed, or windburned lips.

BACKGROUND OF THE INVENTION

Chapped, chafed, or windburned lips are a problem for many women, particularly during the cold months of the year. Chapping is a result of a lack of moisture in surface skin which affects adhesion of surface cells to the skin surface. Thus, chapped skin often appears white and scaly due to detached surface cells.

Chapstick and other lip balms are well known treatments for such conditions. However, lip balms are generally very waxy, unpigmented or minimally pigmented sticks that do not provide any color to the lips. Thus, women who suffer from chapped lips who also wish to wear traditional lipstick, often will apply chapstick either before or after lipstick. This two step process could obviously be made more convenient by formulating lipsticks which, in addition to providing color to the lips, also prevent, retard, or arrest chapping. Generally typical pigmented lipsticks, particularly the new transfer resistant lipsticks, do not provide much protection against chapping. With respect to transfer resistant lipsticks, the high concentration of volatiles quickly flashes off after application to the lips, leaving a film which is considered by some to be somewhat dry.

It is an object of the invention to provide a full color lipstick which prevents, retards, arrests, and ameliorates the effects of chapped lips.

It is a further object of the invention to provide a full color lipstick with an appreciable concentration of volatiles, that prevents, retards, arrests, and ameliorates the effects of chapped lips.

It is a further object of the invention to provide a full color lipstick containing sunscreen which prevents, retards, arrests, and ameliorates the effects of chapped lips.

SUMMARY OF THE INVENTION

The invention comprises a method for preventing, retarding, arresting, or ameliorating the effects of chapped lips comprising applying to the lips a pigmented lipstick composition comprising, by weight of the total composition:
 0.1–30% skin protectant selected from the group consisting of allantoin, cocoa butter, dimethicone, glycerin, petrolatum, shark liver oil, and mixtures thereof,
 1–25% pigment,
 5–85% of an oil selected from the group consisting of nonvolatile oil, volatile oil, and mixtures thereof, and
 3–40% of a wax having a melting point of 30 to 135° C.

DETAILED DESCRIPTION

The term "chap" or "chapping" with respect to lips means chafed, chapped, cracked, or windburned lips. The lipstick compositions used in the method of the invention are "full color lipsticks", which means that they are applied to the lips as a primary lip colorant; as opposed to a non-colored or very minimally colored sticks which do not provide any perceivable color.

The compositions used in the method of the invention comprise 0.1–30%, preferably 0.2–25%, more preferably 0.5–20% of a skin protectant selected from the group consisting of allantoin, cocoa butter, dimethicone, glycerin, petrolatum, shark liver oil, white petrolatum, and mixtures thereof. Preferably the skin protectant used in the method of the invention is dimethicone having a viscosity of 5 to 1,000,000 centipoise at 25° C., more preferably a viscosity of 20 to 600,000 centipoise at 25° C.

The compositions used in the method of the invention contain 1–25%, preferably 1.5–20%, more preferably 2–15% by weight of the total composition of pigment. Suitable pigments include various organic and inorganic pigments. The organic pigments are generally various aromatic types including azo, indigoid, triphenylmethane, anthraquinone, and xanthine dyes which are designated as D&C and FD&C blues, browns, greens, oranges, reds, yellows, etc. Organic pigments generally consist of insoluble metallic salts of certified color additives, referred to as the Lakes. Inorganic pigments include iron oxides, ultramarines, chromium, chromium hydroxide colors, and mixtures thereof.

The compositions used in the method of the invention contain 5–85%, preferably 10–80%, more preferably 20–75% by weight of the total composition of an oil selected from the group consisting of nonvolatile oil, volatile oil, and mixtures thereof.

With respect to the volatile oils, the term "volatile" means that the oil or solvent has a vapor pressure of at least 2 mm. of mercury at 20° C. The viscosity of the volatile solvent is preferably 0.5 to 5 centipoise at 25° C. Such volatile solvents include volatile low viscosity silicone fluids such as cyclic silicones having the formula:

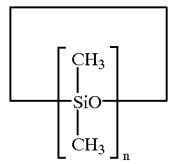

wherein n=3–7. Volatile linear polydimethylsiloxanes are also suitable and generally have from about 2 to 9 silicon atoms and are of the formula:

wherein n=0–7. These silicones are available from various sources including Dow Corning Corporation and General Electric. Dow Corning silicones are sold under the tradenames Dow Corning 244, 245, 344, 345, and 200 fluids. These fluids comprise octamethylcyclotetrasiloxane, decamethylcyclopentasiloxane, hexamethyldisiloxane, or mixtures thereof.

Also suitable as the volatile solvent component are straight or branched chain paraffinic hydrocarbons having 5–20 carbon atoms, more preferably 10–16 carbon atoms. Suitable hydrocarbons are pentane, hexane, heptane, decane, dodecane, tetradecane, tridecane, and $C_{8-20}$ isoparaffins as disclosed in U.S. Pat. Nos. 3,439,088 and 3,818,105, both of which are hereby incorporated by reference. Preferred volatile paraffinic hydrocarbons have a molecular weight of 70 to 190, more preferably 160–180, and a boiling point range of 30 to 320° C., preferably 60 to 260° C., and a viscosity of less than 20 centipoise at 25° C. Such paraffinic hydrocarbons are available from EXXON under the ISOPAR trademark as ISOPAR A, B, C, D, E, G, H, K, L, and M. Similar paraffinic hydrocarbons are also available from Shell Oil under the Shellsol trademark, in particular Shellsol 71; and from Phillips Petroleum under the tradename Soltrol 100, 130, and 220. In addition these paraffinic hydrocarbons may be purchased from Permethyl Corporation under the tradename Permethyl 99A or Permethyl R.

The volatile solvent may be a mixture of volatile silicone and paraffinic hydrocarbons, and if so, a ratio of 1:20 to 20:1 respectively is suggested.

With respect to the nonvolatile oil, the term "nonvolatile" means that the oil has a vapor pressure of less than about 2 mm. of mercury at 20° C. The nonvolatile oil generally has a viscosity of greater than 10 centipoise at 25° C., and may range in viscosity up to 1,000,000 centipoise at 25° C., preferably 100 to 600,000 centipoise at 25° C. Preferably the oil is a liquid to semi-solid at room temperature. Particularly preferred as the nonvolatile oil component is a $C_{12-22}$ fatty ester of citric acid. Preferably the fatty ester of citric acid is formed by the reaction of a $C_{12-22}$ fatty alcohol with citric acid. One, two, or three carboxylic acid groups of the citric acid may be esterified. The fatty acid ester of citric acid generally exhibits the following generic formula:

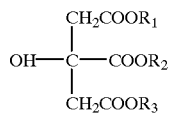

wherein $R_1$, $R_2$, and $R_3$ are each independently H, or a $C_{12-22}$, preferably a $C_{16-22}$ alkyl, more preferably a $C_{18-22}$ alkyl, with the proviso that $R_1$, $R_2$, and $R_3$ cannot all be hydrogen at the same time. Preferably, $R_1$, $R_2$, and $R_3$ are each a $C_{16-22}$ alkyl, preferably isostearyl and the compound is triisostearyl citrate.

Other nonvolatile oils that may be used include esters of the formula RCO—OR' wherein R and R' are each independently a $C_{1-25}$, preferably a $C_{4-20}$ straight or branched chain alkyl, alkenyl or alkoxycarbonylalkyl or alkylcarbonyloxyalkyl. Examples of such esters include isotridecyl isononanoate, PEG-4 diheptanoate, isostearyl neopentanoate, tridecyl neopentanoate, cetyl octanoate, cetyl palmitate, cetyl ricinoleate, cetyl stearate, cetyl myristate, coco-dicaprylate/caprate, decyl isostearate, isodecyl oleate, isodecyl neopentanoate, isohexyl neopentanoate, octyl palmitate, dioctyl malate, tridecyl octanoate, myristyl myristate, octododecanol, and fatty alcohols such as oleyl alcohol, isocetyl alcohol, and the like.

The oil may also comprise naturally occuring glyceryl esters of fatty acids, or triglycerides. Both vegetable and animal sources may be used. Examples of such oils include castor oil, lanolin oil, triisocetyl citrate, $C_{10-18}$ triglycerides, caprylic/capric/triglycerides, coconut oil, corn oil, cottonseed oil, linseed oil, mink oil, olive oil, palm oil, illipe butter, rapeseed oil, soybean oil, sunflower seed oil, walnut oil, and the like.

Also suitable as the oil are synthetic or semi-synthetic glyceryl esters, e.g. fatty acid mono-, di-, and triglycerides which are natural fats or oils that have been modified, for example, acetylated castor oil, glyceryl stearate, glyceryl dioleate, glyceryl distearate, glyceryl trioctanoate, glyceryl distearate, glyceryl linoleate, glyceryl myristate, glyceryl isostearate, PEG castor oils, PEG glyceryl oleates, PEG glyceryl stearates, PEG glyceryl tallowates, and so on.

Also suitable as the oil are nonvolatile hydrocarbons such as isoparaffins, hydrogenated polyisobutene, mineral oil, squalene, petrolatum, and so on.

Straight or branched chain fatty alcohols having the formula R—OH, wherein R is a straight or branched chain saturated or unsaturated alkyl having 6–30 carbon atoms, are also suitable oils. Such fatty alcohols include cetyl alcohol, stearyl alcohol, cetearyl alcohol, and the like.

Also suitable as the oil are various lanolin derivatives such as acetylated lanolin, acetylated lanolin alcohol, and so on.

Also suitable as the nonvolatile oil are various fluorinated oils such as fluorinated silicones, fluorinated esters, or perfluropolyethers. Particularly suitable are fluorosilicones such as trimethylsilyl endcapped fluorosilicone oil, polytrifluoropropylmethylsiloxanes, and similar silicones such as those disclosed in U.S. Pat. No. 5,118,496 which is hereby incorporated by reference. Perfluoropolyethers like those disclosed in U.S. Pat. Nos. 5,183,589, 4,803,067, 5,183,588 all of which are hereby incorporated by reference, which are commercially available from Montefluos under the trademark Fomblin, are also suitable shine enhancers.

Guerbet esters are also suitable oils. The term "guerbet ester" means an ester which is formed by the reaction of a guerbet alcohol having the general formula:

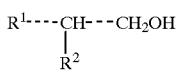

with a carboxylic acid having the general formula:

$R^3COOH$, or $HOOC-R^3-COOH$ wherein $R^1$ and $R^2$ are each independently a $C_{4-20}$ alkyl and $R^3$ is a substituted or unsubstituted fatty radical such as a $C_{1-50}$ straight or branched chain saturated or unsaturated alkyl or alkylene, or phenyl, wherein the substituents are halogen, hydroxyl, carboxyl, and alkylcarbonylhydroxy. Particularly preferred is a carboxylic acid wherein the R group is such to provide an ingredient known as meadowfoam seed oil. Preferably, the guerbet ester is a fluoroguerbet ester which is formed by the reaction of a guerbet alcohol and carboxylic acid (as defined above), and a fluoroalcohol having the following general formula:

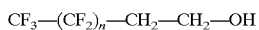

wherein n is from 3 to 40.

Examples of suitable fluoro guerbet esters are set forth in U.S. Pat. No. 5,488,121 which is hereby incorporated by reference. Suitable fluoro-guerbet esters are also set forth in U.S. Pat. No. 5,312,968 which is hereby incorporated by reference. Most preferred is a guerbet ester having the tentative CTFA name fluoro-octyldodecyl meadowfoamate. This ester is sold by Siltech, Norcross Georgia as Developmental Ester L61125A, under the tradename Silube GME-F.

Preferably, the compositions used in the method of the invention comprise:

5–30% of a volatile oil, preferably cyclomethicone,

25–80% of a nonvolatile oil, preferably a $C_{16-22}$ fatty ester of citric acid.

The lipstick compositions used in the method of the invention may contain 3–40%, preferably 5–35%, more preferably 10–30% by weight of the total composition of a wax having a melting point of 30–135° C., and generally includes animal waxes, plant waxes, mineral waxes, silicone waxes, synthetic waxes, and petroleum waxes.

Examples of waxes that can be used include bayberry, beeswax, candelilla, carnauba, ceresin, cetyl esters, hydrogenated jojoba oil, hydrogenated jojoba wax, hydrogenated microcrystalline wax, hydrogenated rice bran wax, japan wax, jojoba butter, jojoba esters, jojoba wax, lanolin wax, microcrystalline wax, mink wax, montan acid wax, montan wax, ouricury wax, ozokerite, paraffin, PEG-6 beeswax, PEG-8 beeswax, rice bran wax, shellac wax, spent grain wax, sulfurized jojoba oil, synthetic beeswax, synthetic candelilla wax, synthetic carnauba wax, synthetic japan wax, synthetic jojoba oil, synthetic wax, stearoxy dimethicone, dimethicone behenate, stearyl dimethicone, and the like, as well synthetic homo- and copolymer waxes from the ethylene series.

The waxes may also be fluorinated waxes, either alone or in addition to the above-mentioned natural or synthetic waxes, such as fluorinated dimethicone copolyols disclosed in U.S. Pat. No. 5,446,114, which is hereby incorporated by reference, having the general formula:

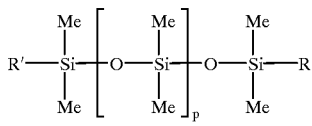

wherein:

p is an integer ranging from 1 to 2,000;

Me is methyl;

R' is $-(CH_2)_3-O-(EO)_a-(PO)_b-(EO)_c-H$;

R is $-(CH_2)_2-(CF_2)_s-CF_3$;

s is an integer ranging from 1 to 13;

a, b, and c are each independently integers ranging from 0 to 20;

EO is $-CH_2CH2-O)-$; and

PO is $-CH_2CH(CH_3)-O-$.

An example of such a fluorinated wax is dimethiconol fluoroalcohol dilinoleic acid, which is sold by Siltech, Inc., under the tradename Silwax F.

Preferred waxes are ethylene homopolymers or ethylene copolymers. The molecular weight of the ethylene homopolymer and/or copolymers used as the wax component may vary, so long as the melting point of the homo- or copolymer either alone or in combination is not greater than 135° C. Generally polyethylene waxes having a melting point range of 30 to 135° C. will have a molecular weight ranging from about 100 and 2,000. Preferably the ethylene copolymers are comprised of ethylene monomer units in either repetitive or randon sequence, in combination with monomer units of the following formula:

$$CH_2=CH-R_1$$

wherein $R_1$ is a $C_{1-30}$ straight or branched chain saturated or unsaturated alkyl, aryl, or aralkyl, preferably a $C_{1-10}$ straight or branched chain alkyl. Examples of ethylene homo- and copolymers which may be used in the invention are set forth in U.S. Pat. No. 5,556,613, which is hereby incorporated by reference.

Preferably the lipsticks used in the method of the invention contain 0.1–20%, preferably 0.5–15%, more preferably 1–10% by weight of the total composition of sunscreen. The term "sunscreen" is defined as an ingredient that absorbs at least 85% of the light in the UV range at wavelengths from 290 to 320 nanometers, but transmits UV light at wavelengths longer than 320 nanometers. Examples of such ingredients include PABA, cinoxide, DEA-methoxycinnamate, digalloyl trioleate, Benzophenone-8, ethyl dihydroxypropyl PABA, Octocrylene, octyl methoxycinnamate, octyl salicylate, glyceryl PABA, homosalate, menthyl anthranilate, benzophenone-3, padimate A, padimate O, phenylbenimidazole sulfonic acid, benzophenone-4, and mixtures of such compounds. Particularly preferred is octyl methoxycinnamate.

Particularly preferred lipsticks for use in the method of the invention comprise, by weight of the total composition:

5–30% cyclomethicone, 0.5–20% dimethicone,

10–30% of a wax having a melting point of 35 to 120° C.

2–15% pigment, and

25–80% of a nonvolatile oil.

The lipsticks may be applied one, two, or more times a day as needed, in lieu of chapstick or lip balm if desired. Use of these lipsticks on a regular basis will reduce, ameliorate, and even prevent chapping of the lips. It is recommended that the lipstick be used for at least one to five days to ameliorate the effects of chapping.

The invention will be further described in connection with the following examples which are set forth for the purpose of illustration only.

EXAMPLE 1

Lipstick compositions were made according to the following formula:

|  | 1 | 2 | 3 |
|---|---|---|---|
| Group 1 Ingredients |  |  |  |
| Synthetic wax | 7.30 | 7.30 | 7.30 |
| Bis-diglyceryl polyacyladipate-2 | 2.00 | 2.00 | 2.00 |
| Triisostearyl citrate | 40.44 | 40.44 | 40.55 |
| Octyl methoxycinnamate | 7.00 | 7.00 | 7.00 |
| Isostearyl alcohol | 1.00 | 1.00 | 1.00 |
| Vitamin E acetate | 0.10 | 0.10 | 0.10 |
| Aloe extract | 0.10 | 0.10 | 0.10 |
| Retinyl palmitate | 0.10 | 0.10 | 0.10 |
| Ascorbyl palmitate | 0.10 | 0.10 | — |
| Methyl paraben | 0.30 | 0.30 | 0.30 |
| Propyl paraben | 0.10 | 0.10 | 0.10 |
| Dimethicone | 1.20 | 1.20 | 1.20 |
| Quaternium-18 hectorite/triisostearyl citrate (20:80) | 1.75 | 1.75 | 1.75 |
| Group 2 Ingredients |  |  |  |
| Titanium dioxide/trioctyldodecyl citrate (50:50) | 10.00 | 4.00 | 8.00 |
| D&C Red 7 Ca Lake/trioctyldodecyl citrate (50:50) | 1.20 | 3.30 | 0.80 |
| FD&C Yellow 5 Al. Lake/trioctyldodecyl citrate (50:50) | 1.10 | 2.80 | 1.60 |
| Iron oxide/trioctyldodecyl citrate (60:40) | 2.00 | 1.75 | 3.33 |
| Iron oxide/trioctyldodecyl citrate (60:40) | 0.30 | 1.95 | 1.33 |
| Group 3 Ingredients |  |  |  |
| Cyclomethicone | 18.00 | 18.00 | 18.00 |
| Trioctyldodecyl citrate | 2.93 | 3.47 | 2.94 |
| Mica | 2.47 | 2.73 | 2.00 |
| Collagen amino acids | 0.01 | 0.01 | — |
| Menthol | 0.50 | 0.50 | 0.50 |

The Group 1 Ingredients were combined and heated to 90° C. with mixing. The Group 2 Ingredients were then added and mixed thoroughly until the batch was uniform. The Group 3 Ingredients were added. The composition was poured into molds and allowed to cool.

EXAMPLE 2

The lipstick compositions of Example 1 were consumer tested with 18 subjects who had normal to dry or dry lips at the beginning of the study. The 18 subjects were instructed not to wear any lip products for six days in order to promote dryness or normalization of the lips in order to simulate chapping. On day 7, the subjects chose a lipstick from the three available shades, Mauve, Wine, and Nudity, which were 1, 2, and 3 respectively, from Example 1. Subjects were asked to apply the test lipstick a minimum of two times per day for the next five days. On day 12 subjects were asked to apply the lipstick and rate wear at 2, 4, and 6 hours. After 6 hours of wear on day 12, subjects removed the lipstick and were asked to answer several questions. The following results were obtained:

| INITIAL APPLICATION | % Subjects Who Agreed |
| --- | --- |
| Lips feel conditioned | 89 |
| Soothes lips | 100 |
| Lips feel moisturized | 94 |

| 2-HOUR WEAR | % Subjects Who Agreed |
| --- | --- |
| Lips feel moisturized | 83 |
| Helps condition lips | 83 |
| Prevents dryness | 94 |
| Helps improve and maintain healthier lip condition | 94 |

| 4-HOUR WEAR | % Subjects Who Agreed |
| --- | --- |
| Lips feel moisturized | 78 |
| Helps condition lips | 83 |
| Soothes lips | 83 |
| Prevents dryness | 94 |
| Helps improve and maintain healthier lip condition | 94 |

| 6-HOUR WEAR | % Subjects Who Agreed |
| --- | --- |
| Smoothes lips | 67 |
| Lips feel moisturized | 67 |
| Helps condition lips | 72 |
| Soothes lips | 67 |
| Prevents dryness | 72 |
| Helps improve and maintain a healthier lip condition | 78 |

After the 6 hour wear test was completed, the subjects were asked to remove the lipstick and answer the following questions:

| Do your lips feel . . . | % Subjects Who Agreed |
| --- | --- |
| Smooth | 56 |
| Moisturized | 56 |
| Conditioned | 50 |
| Dry | 22 |
| Chapped | 11 |
| Comfortable | 67 |
| Uncomfortable | 11 |

Only 11% of the subjects who started the testing with normalized lips reported that their lips felt chapped at the end of the study.

EXAMPLE 3

The lipstick compositions of Example 2 were tested with 19 subjects who were selected based upon their perception that they had dry or chapped lips. Subjects chose from the three available lipstick shades, Mauve, Wine, and Nudity; which were 1, 2, and 3 respectively, from Example 1. Subjects were asked to apply the test lipstick a minimum of two times per day for five days. On day 12, subjects were asked to apply the lipstick and rate wear at 2, 4, and 6 hours. After 6 hours of wear on day 12, subjects were asked to remove their lipstick and answer several questions. The results are as follows:

| INITIAL APPLICATION | % Subjects Who Agreed |
| --- | --- |
| Lips feel conditioned | 89 |
| Soothes lips | 79 |
| Lips feel moisturized | 95 |

| 2-HOUR WEAR | % Subjects Who Agreed |
| --- | --- |
| Lips feel moisturized | 100 |
| Helps condition lips | 95 |
| Prevents dryness | 95 |
| Helps improve and maintain healthier lip condition | 95 |

| 4-HOUR WEAR | % Subjects Who Agreed |
| --- | --- |
| Lips feel moisturized | 89 |
| Helps condition lips | 89 |
| Soothes lips | 84 |
| Prevents dryness | 84 |
| Helps improve and maintain healthier lip condition | 84 |

| 6-HOUR WEAR | % Subjects Who Agreed |
| --- | --- |
| Smoothes lips | 79 |
| Lips feel moisturized | 79 |
| Helps condition lips | 79 |
| Soothes lips | 79 |
| Prevents dryness | 84 |
| Helps improve and maintain a healthier lip condition | 84 |

After the 6 hour wear test was completed, the subjects were asked to remove the lipstick and answer the following questions:

| Do your lips feel . . . | % Subjects Who Agreed |
| --- | --- |
| Smooth | 74 |
| Moisturized | 63 |
| Conditioned | 63 |
| Dry | 11 |
| Chapped | 0 |
| Comfortable | 68 |
| Uncomfortable | 0 |

None of the subjects who participated in the study based upon their perception that they had dry lips, stated that their lips were chapped at the end of the study.

EXAMPLE 4

A total of 18 subjects, after having refrained from using any lip products for 6 days, participated in the study. Dry lips were simulated by blowing a stream of dry air over the lips for thirty seconds. Baseline readings for lip moisture were performed on dry lips using a Nova Dermal Phase Meter fitted with a lip probe. Baseline lower lip replicas for lip smoothing were prepared using SILFLO rubber impression material. Trained evaluator clinical evaluations for upper and lower lip dryness, roughness, flaking, cracking, and fine lines were recorded.

After baseline readings, subjects were instructed to apply a product of their color choice selected from 1, 2, and 3, in Example 1, in an amount sufficient to cover the lips. Subjects were asked to refrain from licking their lips prior to the 15 minute reading. After 15 minutes, the lipstick was wiped from the lips and readings were performed. Subjects were then asked to continue using the product for 5 days and return to the laboratory for final evaluation. The following results were obtained:

% Improvement in Lip Smoothing After 5 Days of Use

| Mean | Standard Deviation |
|------|--------------------|
| 67.71 | 6.88 |

The above results are significant at the 95% confidence level.

% Improvement in Moisture

| Immediate | | After 5 Days | |
|---|---|---|---|
| Mean | St. Dev. | Mean | St. Dev. |
| 140.8 | 34.39 | 166.0 | 29.96 |

The above results are significant at the 95% confidence level.

Clinical Evaluation of Lip Condition

| Baseline | | After 5 days | | | |
|---|---|---|---|---|---|
| Mean | St. Dev. | Mean | St. Dev. | | |
| 1.00 | 0.16 | 0.81 | 0.10 | Dryness, upper lip | |
| 1.21 | 0.15 | 0.93 | 0.13 | Dryness, lower lip | B |
| 1.07 | 0.07 | 0.53 | 0.13 | Roughness, upper lip | A |
| 1.27 | 0.12 | 0.73 | 0.18 | Roughness, lower lip | A |
| 0.20 | 0.11 | 0.20 | 0.11 | Flaking, upper lip | |
| 0.40 | 0.16 | 0.27 | 0.12 | Flaking, lower lip | |
| 0.53 | 0.17 | 0.20 | 0.11 | Cracking, upper lip | B |
| 0.73 | 0.18 | 0.60 | 0.16 | Cracking, lower lip | |
| 1.00 | 0.00 | 1.00 | 0.00 | Fine lines, upper lip | |
| 1.00 | 0.00 | 1.00 | 0.00 | Fine lines, lower lip | |

Scoring: absent = 0, mild/slight = 1, moderate = 2, severe = 3.
A = significant improvement at 95% confidence level.
B = significant improvement at 90% confidence level.

The above results show that treatment of the lips with the lipstick compositions mentioned herein provide improvements in lip condition.

While the invention has been described in connection with the preferred embodiment, it is not intended to limit the scope of the invention to the particular form set forth, but, on the contrary, it is intended to cover such alternatives, modifications, and equivalents as may be included within the spirit and scope of the invention as defined by the appended claims.

We claim:

1. A method for treating the effects of chafed, chapped, cracked, or windburned lips comprising applying to the lips a pigmented lipstick composition comprising, by weight of the total composition:

0.5–20% of a skin protectant selected from the group consisting of allantoin, cocoa butter dimethicone, glycerin petrolatum shark liver oil, and mixtures thereof, 2–15% pigment 5–30% of a volatile oil having a viscosity of 0.5 to 5 centipoise at 25° C., selected from the group consisting of cyclomethicone, straight or branched chain paraffinic hydrocarbons having 5 to 20 carbon atoms, and mixtures thereof, 5–80% of a nonvolatile oil having the formula

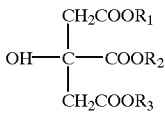

wherein $R_1$, $R_2$ and $R_3$ are each independently a $C_{12-22}$ alkyl, and

3–40% of a wax having a melting point of 30 to 135° C.

2. The method of claim 1 wherein the wax is an ethylene homopolymer or ethylene copolymer.

3. They method of claim 1 wherein the skin protectant is dimethicone.

4. The method of claim 1 wherein the lipstick additionally comprises 0.1–20% by weight of the total composition of sunscreen.

5. The method of claim 1 wherein the lipstick is applied once per day.

6. The method of claim 1 wherein the lipstick is applied twice per day.

7. The method of claim 1 wherein the volatile oil is cyclomethicone.

8. The method of claim 3 wherein the dimethicone has a viscosity of 10 to 1,000,000 centipoise at 25° C.

* * * * *